United States Patent [19]
Robinson et al.

[11] Patent Number: 6,069,119
[45] Date of Patent: *May 30, 2000

[54] METHOD FOR PREPARING AN ALKALINE EARTH METAL TALLATE

[75] Inventors: Peter M. Robinson; Robert E. Brooks, both of High Point; Terry E. Singleton, Jamestown, all of N.C.

[73] Assignee: High Point Chemical Corp., High Point, N.C.

[*] Notice: This patent is subject to a terminal disclaimer.

[21] Appl. No.: 09/024,591

[22] Filed: Feb. 17, 1998

Related U.S. Application Data

[63] Continuation of application No. 08/666,902, Jun. 20, 1996, Pat. No. 5,763,373.

[51] Int. Cl.$^7$ ............................................. C10M 105/22
[52] U.S. Cl. ............................................. 508/449; 162/5
[58] Field of Search .................. 508/449; 162/5; 516/75

[56] References Cited

U.S. PATENT DOCUMENTS

| | | | |
|---|---|---|---|
| Re. 20,709 | 4/1938 | Lister | 508/449 |
| 2,399,063 | 4/1946 | Schantz | 508/449 |
| 3,951,676 | 4/1976 | Elste, Jr. | 106/277 |
| 4,282,387 | 8/1981 | Olstowski et al. | 568/618 |
| 5,417,807 | 5/1995 | Fossas et al. | 162/5 |
| 5,763,373 | 6/1998 | Robinson et al. | 508/449 |

*Primary Examiner*—Margaret Medley
*Attorney, Agent, or Firm*—Bruce F. Jacobs

[57] ABSTRACT

A stable, fluid alkaline earth metal tallate dispersion is prepared by (i) forming a pre-emulsion of fatty acids derived from tall oil, water, and a surfactant; (ii) forming an alkaline earth metal salt dispersion from an alkaline earth metal oxide and/or hydroxide, a lower carboxylic acid, and water; and (iii) incorporating the pre-emulsion into the alkaline earth metal salt dispersion under high shear and low pressure.

26 Claims, 3 Drawing Sheets

METHOD FOR PREPARING AN ALKALINE EARTH METAL TALLATE

This is a continuation of application Ser. No. 08/666,902 filed on Jun. 20, 1996, now U.S. Pat. No. 5,763,373.

FIELD OF THE INVENTION

The present invention is directed to a method for preparing a composition containing an alkaline earth metal tallate, more specifically a calcium tallate which exhibits improved performance in the field of deinking, specifically flotation deinking.

BACKGROUND OF THE INVENTION

Deinking is the process of removing ink and other contaminants from waste paper. There are two main techniques in current use: "flotation" and "wash" deinking processes. In "flotation deinking" an aqueous suspension of waste paper pulp fibers, ink, and other non-cellulosic contaminants is formed and then air is mixed into the suspension. In the presence of appropriate additives, air bubbles selectively attach to ink particles and carry the particles to the surface of the aqueous suspension, thereby forming an ink rich froth. The froth is then removed, leaving behind a relatively ink-free fiber slurry. Flotation deinking processes are especially useful in removing hydrophobic inks with particle sizes larger than about 10 $\mu$m. The additives used in such processes are generally specialty surfactants or fatty acid soaps, and/or combinations of the same which are intended to collect the detached ink particles and to agglomerate any relatively finer ink particles to increase removal efficiency in the flotation stage. The presence of additives that disperse the ink particles rather than agglomerate them is considered detrimental to the effectiveness of the flotation stage. "Wash deinking," on the other hand, is particularly useful when the ink and other particles being removed are finely dispersed so that the particles are smaller than about 5 $\mu$m. This requires the addition of ink emulsifying surfactants/dispersants so that when a dilute waste paper pulp slurry is thickened, the fine inks will tend to stay with the water being removed rather than reattaching to the pulp fibers. Thus, a relatively clean pulp is produced.

Conventional methods for preparing alkaline earth metal tallates entail a one-step reaction of an alkaline earth metal hydroxide, e.g. calcium hydroxide, with tall oil fatty acids. Oftentimes, this has been done in situ during deinking by the addition of unneutralized tall oil fatty acids (TOFA) in the presence of water having high hardness, c.f. U.S. Pat. No. 5,417,807. In such a case, calcium salts are formed by reaction of the tall oil fatty acids with the calcium ions present in the hard water. When the water hardness was too low, additional calcium ions are provided by the addition of a salt such as calcium chloride to the water along with the tall oil fatty acids. Calcium salts of the fatty acid(s) provide a preferred bubble size/configuration for flotation.

Calcium stearate salts are known deinking agents which are usually prepared by combining calcium hydroxide and stearic acid under controlled conditions at a suitable temperature and mixing them in a high speed mixer.

Conventional preparative procedures, however, have failed to produce sufficiently effective deinking compositions from tall oil fatty acids. Specifically, conventionally prepared compositions from calcium hydroxide and tall oil fatty acids, i.e. calcium tallate dispersions, have heretofore suffered from one or more of the following problems: (i) they have not been stable for a commercially acceptable period of time; (ii) they have exhibited undesirable particle size distributions; and (iii) they have exhibited poor fluidity, i.e. upon aging the viscosity of the dispersions increases to a nonpumpable gel.

It is thus an object of the present invention to prepare an alkaline earth metal tallate having improved stability, desirable particle distributions, and good fluidity.

SUMMARY OF THE INVENTION

The present invention uses a double displacement process for preparing an alkaline earth metal tallate dispersion by (i) forming a pre-emulsion of tall oil fatty acids, water, and surfactant; (ii) separately forming an alkaline earth metal salt dispersion from an alkaline earth metal oxide or hydroxide, an organic acid having a pKa ranging from about 2 to about 6, and water, and (iii) incorporating the pre-emulsion into the alkaline earth metal salt dispersion under conditions of high shear and low pressure.

DESCRIPTION OF THE PREFERRED EMBODIMENTS

Figure 1:
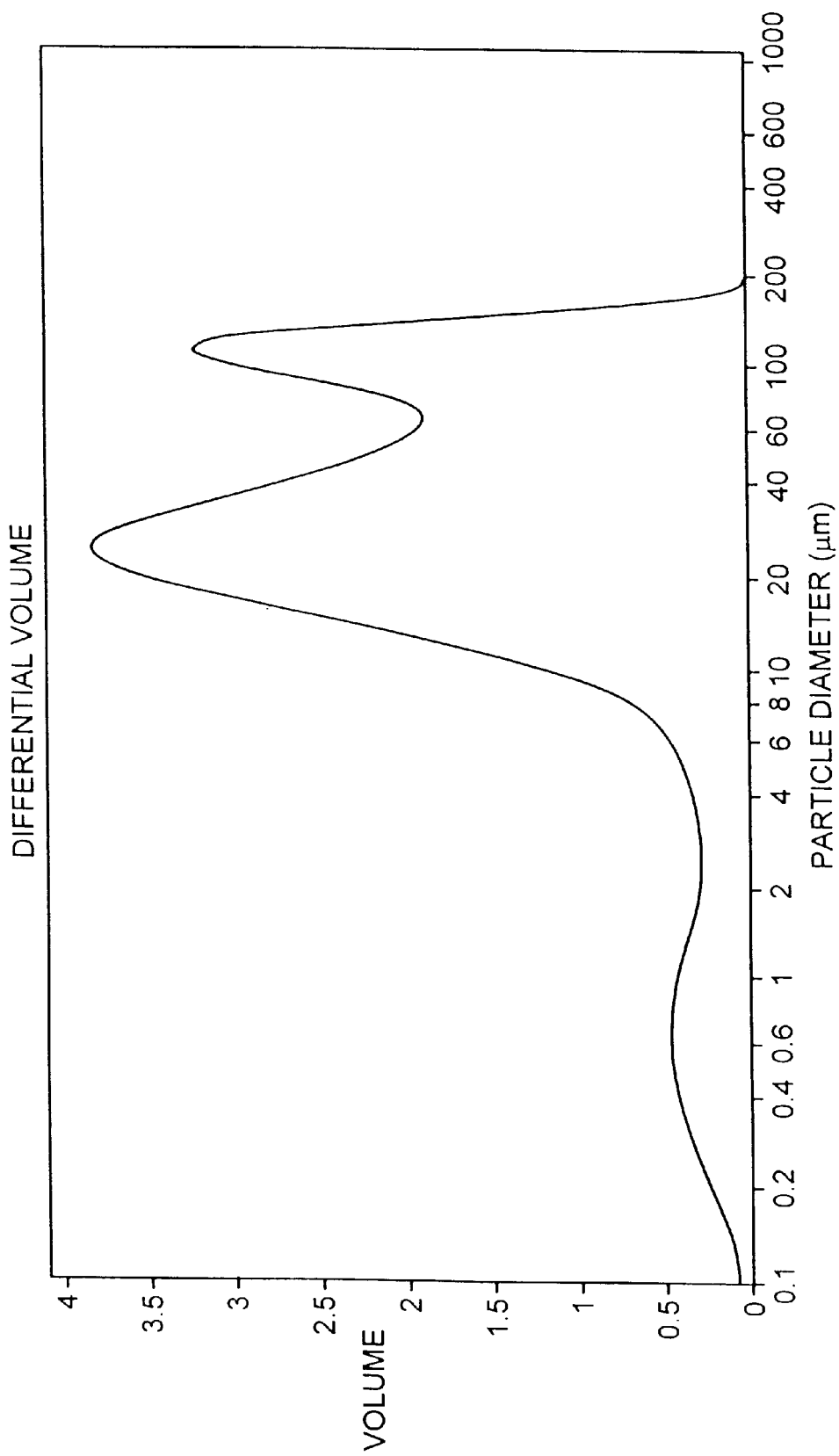
FIG. 1 is a graph showing a preferred bimodal particle size distribution of an alkaline earth metal tallate dispersion prepared in accordance with the present invention.

The present invention uses a double displacement process for preparing an alkaline earth metal tallate dispersion by (i) forming a pre-emulsion of a tall oil fatty acid, water, and a surfactant; (ii) forming separately an alkaline earth metal salt dispersion from an alkaline earth metal oxide or hydroxide, an organic acid having a pKa ranging from about 2 to about 6, and water and (iii) incorporating the pre-emulsion into the alkaline earth metal salt dispersion under conditions of high shear and low pressure. More particularly, the pre-emulsion is formed from those tall oil fatty acids present in partially de-rosinated tall oil, water, and a surfactant. Also more particularly, the organic acid is a lower carboxylic acid.

The term "tall oil fatty acids" is used herein to refer to the mixture of fatty acids which are naturally occurring in tall oil. More specifically, the acids are generally of the formula $R^5COO-M$ wherein $R^5$ is a linear, branched, or cyclic alkyl or alkenyl group having about 14 to about 20 carbon atoms and wherein M is hydrogen or a counter-ion such as K, Na or Ca. Tall oil fatty acids are generally present in the pre-emulsion in an amount from about 15 to 45 wt %, preferably from about 20 to 40 wt %, and more preferably from about 25 to 30 wt %, based upon the total weight of the desired final product. The primary acids in the tall oil fatty acids have been reported to be about 45 wt % oleic acid, about 40 wt % linoleic acid, and up to about 15 wt % rosin acid. Preferably, the tall oil fatty acids are obtained by partially derosinating tall oil in a conventional manner.

The surfactant used to form the pre-emulsion is any surfactant which is capable of decreasing the interfacial tension between the oil (fatty acids) and water sufficiently that a stable pre-emulsion can form. While any conventional surfactant may be used, it is preferable that the surfactant be a non-ionic alkoxylated compound represented by the formula:

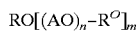
$$RO[(AO)_n-R^O]_m$$

wherein R is selected from the group consisting of (a) linear and branched alkyl and alkenyl groups having about 8 to about 22 carbon atoms; (b) $R^1CO-$ wherein $R^1$ is a linear or branched alkyl or alkenyl group having about 7 to about 24 carbon atoms; (c) $(R^2)_aC_6H_{(5-a)}$— wherein $R^2$ is a linear or branched alkyl and alkenyl group having about 7 to 24 carbon atoms and "a" is 0 or 1; (d) a group derived from a linear, branched, and cyclic aliphatic polyol having from about 2 to 14 carbon atoms; and (e) a group derived from a linear, branched, and cyclic aliphatic diacid having about 8 to 20 carbon atoms; AO is an oxyalkylene group having 2 to about 4 carbon atoms or a mixture of such groups in random or block configuration; $R^O$ is selected from the group consisting of H, $R^1$ and $R^1CO$; n is a number from about 5 to about 150; and m is an integer from about 1 to 6.

Suitable polyols useful for preparing the preferred surfactant include, for example, ethylene glycol, propylene glycol, trimethylene glycol, butylene glycol, glycerol, trimethylol propane, trimethylol ethene, 1,2,4-butanetriol, 1,2,6-hexanetriol, 1,1,1-trimethylol hexane, pentaerythritol, diglycerol, and sorbitol. Suitable diacids include, for example, octanedioic (suberic), nonanedioic (azelaic), hexadecanedioic (thapsic), octadecanedioic, and heneicosanedioic (japanic) acids.

Such surfactants are commercially available and may be made by techniques well known in the art. Specific examples of such surfactants include (i) the Neodol® surfactants, e.g. Neodol® 1-3, Neodol® 1-5, Neodol® 1-7 and Neodol® 1-9 from Shell Chemical, which are $C_{11}$ alcohols which have been ethoxylated with 3, 5, 7, and 9 moles of ethylene oxide, respectively; (ii) Kao Emulgen® 150 surfactant with $C_{12}$ alcohols with 50 moles of ethylene oxide, available from Kao Corporation, Japan; (iii) Hipochem® CO-130, a surfactant which contains castor oil with about 130 moles of ethylene oxide, available from High Point Chemical Company, High Point, N.C.

More preferably, a binary surfactant system is used. Most preferably, a combination of Neodol® 1-3 and Neodol® 1-7 is used.

The surfactant component is generally used in the present invention in an amount of from about 1 to 10 wt % based on the weight of the pre-emulsion, preferably from about 1.5 to 6 wt %, and more preferably from about 5 to 6 wt %.

In addition to the tall oil fatty acids, surfactant, and water, the pre-emulsion may contain additional materials. For example, the pre-emulsion may contain rosin acids, i.e. alkylated, tricyclic, unsaturated organic acids, which are naturally present in tall oil. The two main rosin acids in tall oil are abietic acid and pimaric acid. Generally, the pre-emulsion will contain rosin acids in an amount up to about 15 wt %, more preferably about 1 to about 10 wt %, and even more preferably about 5 wt % to about 10 wt %, based upon the weight of all the tall oil fatty acids.

Furthermore, the pre-emulsion may also contain an anionic surfactant such as dodecylbenzene sulfonate, fatty acid products such as Diacid 1575 or Diacid 1550 (combinations of $C_{18}$-monomer fatty acid, $C_{21}$ fatty acid lactone, and $C_{36}$ dimer fatty acid) available from Westvaco Chemicals and stearic acid, where amounts of each range from about 1 to 10 wt %, preferably 1 to 5 wt % based on the total weight of the pre-emulsion. Other fatty acids having about 8 to about 22 carbon atoms may be added to optimize the deinking performance of the resulting composition for specific paper mills. Also, monomer acids and dimer acids may be included in the pre-emulsion in an amount ranging up to about 50 wt % of the tall oil fatty acids in the pre-emulsion. Organic acids having between about 16 and about 22 carbon atoms, may also be present, especially when the alkaline earth metal tallate is to be used for deinking.

The pre-emulsion is formed by mixing tall oil fatty acids, the surfactant (or surfactants), water, and any other suitable materials until a substantially homogenous pre-emulsion is formed. Any suitable mixing device may be used provided that it can form a pre-emulsion. Preferably, a high shear, low pressure Silverson in-line mixer (homogenizer), available from Silverson Machines Inc., East Longmeadow, Mass., is used. When the pre-emulsion ingredients are mixed in such a mixer, they rotate intensely so that a suction results and liquid and solid materials are drawn upwards from the bottom of the mixing vessel. A rotor, typically consisting of three or four sets of finely machined teeth that run concentrically against three or four sets of stators, subjects the ingredients to millions of individual shearing actions per second, providing intense shear. The Silverson mixer appears to generate less heat and a smaller heat rise than do many other mixers. It is believed that the low generation of heat during the mixing may be beneficial to preparing the stable alkaline earth metal tallate dispersions of this invention.

The pre-emulsion so formed is inherently stable, i.e. it is sufficiently stable that it can be prepared and stored for up to about 10 days before being used to form the alkaline earth metal tallate dispersion. When stored prior to use, the pre-emulsion is preferably maintained at a temperature of about 15 to about 30° C.

The salt dispersion is a highly alkaline aqueous dispersion prepared from an acid and a base which, when combined with the pre-emulsion according to the specific manner of this invention, forms the improved alkaline earth metal tallate dispersions of this invention. The acids useful for preparing the salt dispersion are weak acids having a pKa value of about 2 to less than 6. Suitable such acids include the lower carboxylic acids, e.g. formic acid, hydroxy acetic acid, peracetic acid, propionic acid, butyric acid, and the like. Acetic acid, is the currently preferred lower carboxylic acid. Suitable acids also include chloro acids such as chloroacetic acid, 2-chloropropionic acid, 3-chloropropionic acid, and 4-chlorobutyric acid. For example, the following acids have the indicated corresponding pKa values: formic acid (3.77), acetic acid (4.76), propionic (4.88), butanoic acid (4.82), nonanoic acid (4.95), chloroacetic acid (2.86), 2-chlorobutyric acid (2.84), 3-chlorobutyric acid (4.06), 4-chlorobutyric acid (4.52), hydroxy acetic acid (3.83), malonic acid (2.83), phenyl acetic acid (4.31), vinyl acetic acid, or 3-butanoic acid (4.35). Preferably, the acids contain about 12 carbon atoms or less. More preferably, the acids contain less than 10 carbon atoms. Generally, the amount of acid added to form the salt dispersion is from about 0.5 to about 1.0 wt %, based on the weight of the salt dispersion.

An alkaline earth metal oxide or hydroxide or mixture thereof is used as the base. The preferred bases are hydrated lime and calcium oxide. The base is present in excess of the stoichiometric amount required to neutralize the acid, preferably in at least 25% excess, more preferably at least 100% excess, and most preferably at least about 1000% excess.

The resulting salt dispersion thus contains salts containing an alkaline earth metal. Examples of such salts include calcium acetate, calcium propionate, calcium butyrate, magnesium acetate, barium propionate, and the like. The salt dispersion generally has a pH of about 12 or higher.

The salt dispersion is formed by mixing the acid and alkaline earth metal oxide or hydroxide, and water by any method which produces a dispersion, i.e. conventional stirring techniques. While the mixing may be performed at any temperature, a temperature that is less than about 55° C., less than about 50° C., or less than about 45° C. may be more suitable. Even more preferably a temperature of less than 40° C., preferably less than about 35° C., and even more preferably less than about 30° C., is used because these temperatures permit the salt dispersion to be used immediately upon formation and without cooling.

It is believed that maintaining the temperature below about 40° C. during neutralization, high shear mixing (i) minimizes the exposure of the tall oil fatty acid particles to conditions likely to form sticky agglomerates, and (ii) also enhances product fluidity by rapidly cooling the salt dispersion as quickly as it is formed.

Figure 2:
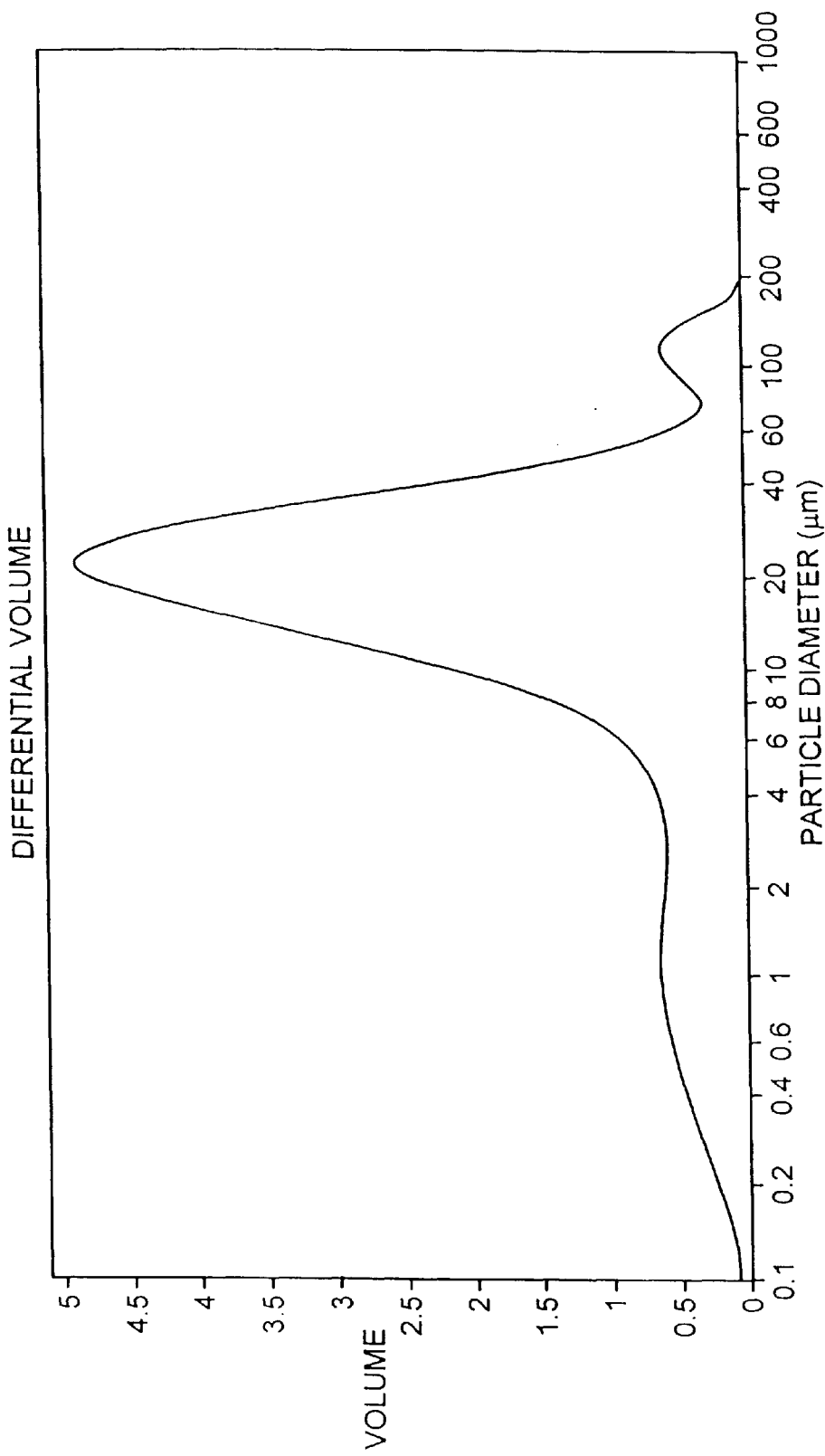
FIG. 2 is a graph showing a normal particle size distribution of a conventionally prepared alkaline earth metal tallate composition.

To complete the manufacture of the alkaline earth metal tallate dispersion, a pre-emulsion as described above is incorporated into a salt dispersion with mixing (homogenization) being performed under conditions of high shear and low pressure. The shear must be sufficiently high and the pressure sufficiently low to generate sufficient turbulence to produce a stable alkaline earth metal tallate dispersion. A suitable mixing device is a high shear low pressure mixer such as the Silverson in-line mixer (homogenizer) described previously. The high shear, low pressure mixing continues until a uniform alkaline earth metal tallate dispersion forms. The maximum temperature to which the system is exposed during the mixing should be less than about 55° C., preferably less than about 50° C., and even more preferably less than about 45° C. The mixing is performed at a sufficiently low rate of addition and pressure that the temperature does not exceed the temperature maximum. Generally this can be accomplished by starting with a pre-emulsion at room temperature and then using a mixing pressure of below about 20 psig, more preferably below about 15 psig. The mixing continues for a limited time to minimize the formation of sticky agglomerates, contaminant gels, and the like, which cause product degradation and reduce product stability. The high shear causes the sizes of the pre-emulsion particles to be reduced sufficiently to form the stabilized alkaline earth metal tallate dispersions. Preferably, the high shear results in the formation of a bimodal particle size distribution, i.e. a particle size distribution containing two clear maxima. Most preferably one maxima is in the range of about 10 to about 30 microns and a second is from about 100 to about 150 microns. FIG. 1 shows such a distribution while FIG. 2 shows a distribution having a single maxima of about 20 microns resulting from an alkaline earth metal tallate composition prepared using a Gaulin-type homogenizer. Preferably, the particle size maxima are in the ranges of (i) from about 15 to about 25 microns and (ii) from about 100 to about 125 microns.

The double displacement method of the present invention results in a smooth controllable reaction occurring at low viscosity with excellent heat exchange properties. A product having good long term stability, i.e. 4 to 6 months at a maximum temperature up to 30° C., is obtained without post-formation stabilizer addition.

When it is expected that the alkaline earth metal tallate dispersions may be exposed to elevated temperatures during storage prior to use, e.g. during summer, post-formation stabilization is recommended. Suitable stabilizers are anionic, cationic, or nonionic surfactants. Examples of specific such post-formation stabilizers include dicarboxylic acids, sulfonates, ether carboxylates, quaternary ammonium compounds, and EO:PO block and random polymeric surfactants. Specific currently preferred post-formation stabilizers include dodecylbenzene sulfonate, the dicarboxylic acid Diacid 1575 and a sulfonated naphthalene-formaldehyde condensate, Daxad 16 (Hampshire Chemical, Lexington, Mass. as well as ether carboxylates NEODOX® 91-5, NEODOX® 91-7, NEODOX® 1-4, NEODOX® 23-4, NEODOX® 23-6, NEODOX® 25-6, and NEODOX® 25-11, NEODOX® 45-7 from Shell Chemical, and benzyl trimethyl ammonium chloride. The post-formation stabilizers are generally used in an amount of about 0.5 to 2.5 wt % based on the weight of the alkaline earth metal tallate dispersion, preferably in an amount of about 0.5 to about 1 wt % thereof. The stabilizers may be incorporated into a previously prepared dispersions by any conventional mixing equipment. The stabilizers have been found to increase the stability of the dispersions at maximum temperatures of about 45° C. to about 50° C. from less than about 10 days to more than 90 days.

The following examples illustrate the invention described herein. All parts and percents are by weight unless otherwise specified.

EXAMPLE 1

A calcium tallate dispersion was prepared. First, a pre-emulsion was prepared from 963.9 parts of a tall oil fatty acid mixture, 837.5 parts water, and a binary surfactant system of 36.1 parts Neodol® 1-3 and 71.8 parts Neodol® 1-7. The ingredients were mixed in a Silverson mixer (Model No 450LS) for about 30 minutes at room temperature.

A calcium acetate salt dispersion was prepared by mixing 11.9 parts of acetic acid, 1316.3 parts of water, and 263.2 parts hydrated lime at 20° C. The resulting dispersion had a beige color and separated upon standing, i.e. without agitation.

The pre-emulsion, which had been prepared the day previously, had been stored at room temperature and was incorporated into the salt dispersion by continuously adding the pre-emulsion to the stirred and cooled calcium dispersion for about 60 to 75 minutes and subsequently homogenizing by means of a Silverson in-line high shear low pressure homogenizer. The homogenization lasted for a total of about 30 minutes with 5 passes through the homogenizer.

The resulting alkaline earth metal tallate dispersion demonstrated excellent stability at room temperature, desirable particle distributions, and good fluidity. The dispersion was free-flowing, had a bi-modal particle size distribution with a first maxima at about 10 to 30 microns and a second at about 90 to 110 microns, and was stable for up to 180 days, at a temperature of 25–30° C. during which time the bi-modal particle size distribution was retained. The initial viscosity was 50 to 100 cps, and the viscosity remained at about 150 to 300 cps, and did not increase to more than 500 cps.

COMPARATIVE EXAMPLE A

A pre-emulsion and a salt dispersion are prepared according to Example 1 with the exception that the pre-emulsion is incorporated into the salt dispersion by means of high pressure mixing devices which cause the temperature of the material being mixed to increase substantially. The two mixers are (i) a Gaulin high shear, high pressure mixer available from Manton Gaulin Manufacturing Co., Everett, Mass., and (ii) a Tekmar mixer, a high shear, medium pressure mixer available from Tekmar Co., Cincinnati, Ohio. The Gaulin mixer is designed to operate at pressures as high as more than 20,000 psig and generates its shear action by means of extrusion. The Tekmar mixer is intended to operate at medium pressures of about 40 to 100 psig and generates its shear action by means of both cutting and extrusion. Both the Gaulin and Tekmar mixers generate a greater heat rise during processing than does the Silverson mixer.

The tallate dispersion produced with a Gaulin mixer operating at a pressure of about 4,000 psig is initially stable and has a desirable bimodal particle size distribution. However, unacceptable fluid properties and storage stability profiles are observed. Within 30 days at 25–30° C., the viscosity increased from an initial value of about 65–120 cps to more than 600 cps and oftentimes to total gelation.

An attempt to produce a tallate dispersion with a Tekmar mixer operating at a pressure of about 40 to about 60 psig was unsuccessful due to the generation of gels during the processing.

Figure 3:
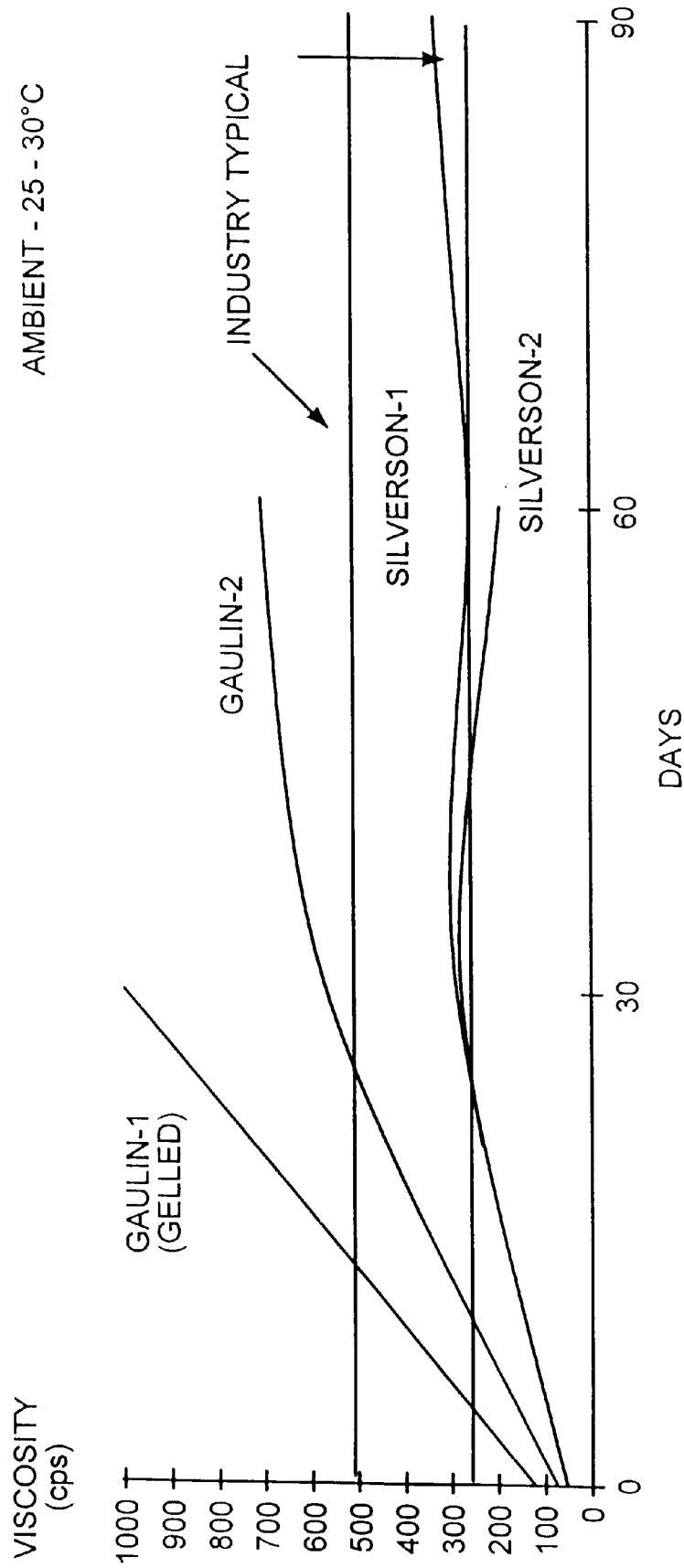
FIG. 3 is a stability graph showing stability characteristics of various calcium tallate dispersions.

FIG. 3 is a stability graph comparing stability characteristics of two calcium tallate dispersions prepared in accordance with Example 1 and two other dispersions prepared with the Gaulin mixer of this Comparative Example A.

COMPARATIVE EXAMPLE B

A pre-emulsion was prepared according to Example 1. The individual ingredients, i.e. the acetic acid and hydrated lime, of the salt dispersion of Example 1 were added to the pre-emulsion separately and the resulting mixture subsequently processed as in Example 1 using a Silverson in-line high shear low-pressure mixer. The resulting dispersion which formed exhibited adverse gel formation and was inferior in quality. This experiment demonstrates the benefit of the initial preparation of the salt dispersion and the double displacement preparation method of the present invention.

EXAMPLE 2

A calcium tallate dispersion as in Example 1 was prepared. The dispersion was post-formation stabilized by the addition of 1 wt % of one of each of the following stabilizers: dodecylbenzene sulfonic acid, Diacid 1575, and Diacid 1550. Each of the stabilizers was incorporated into a tallate dispersion by conventional simple mixing after completion of the homogenization.

The post-formation stabilized dispersions exhibited excellent stability at temperatures up to about 50° C. After 60 and 90 days, the viscosity of each of the dispersions remained below 500 cps even when subjected to temperatures ranging from a high of about 50° C. to a low of about 25° C.

What is claimed is:

1. A double displacement method for preparing an alkaline earth metal tallate dispersion of enhanced stability comprising the steps of (i) forming a pre-emulsion of tall oil fatty acids, water, and surfactant; (ii) separately forming an alkaline earth metal salt dispersion from an organic acid having a pKa of from about 2 to about 6, an alkaline earth metal compound selected from the group consisting of oxides, hydroxides, and mixtures thereof, and water; and (iii) incorporating the pre-emulsion into the alkaline earth metal salt dispersion under conditions of high shear and low pressure.

2. The method of claim 1, wherein the tall oil fatty acids are partially de-rosinated tall oil.

3. The method of claim 1, wherein the alkaline earth metal compound is calcium oxide.

4. The method of claim 1, wherein the alkaline earth metal compound is calcium hydroxide.

5. The method of claim 1, wherein the tall oil fatty acids are present in an amount of about 15 to about 45 wt % based upon the total weight of the alkaline earth metal tallate dispersion.

6. The method of claim 1, wherein the pre-emulsion further contains rosin acids naturally present in tall oil in an amount ranging from about 1 to about 15% by weight, based upon the weight of the tall oil fatty acids.

7. The method of claim 1, wherein the pre-emulsion further contains at least one component selected from the group consisting of stearic acid, monomer acid, and dimer acid.

8. The method of claim 1, wherein the surfactant is present in the pre-emulsion in an amount of about 1 to 10 wt % based on the weight of the pre-emulsion.

9. The method of claim 8, wherein the surfactant is a mixture of alkoxylated alcohols.

10. The method of claim 1, wherein the pre-emulsion has sufficient stability to be stored for 30 days at a temperature of about 10 to about 30° C. before incorporation into the salt dispersion.

11. The method of claim 1, wherein the organic acid contains from 1 to about 12 carbon atoms.

12. The method of claim 1, wherein the organic acid is selected from the group consisting of formic, acetic, propionic, butyric, valeric, hexanoic, heptanoic, octanoic, nonanoic, decanoic, undecanoic, dodecanoic, hydroacetic, malonic, phenylacetic, vinylacetic, chloroacetic, 2-chloropropionic, 3-chloropropionic, and 4-chlorobutyric acids.

13. The method of claim 12, wherein the organic acid is acetic acid.

14. The method of claim 1, wherein the organic acid is added to form the salt dispersion in an amount of about 0.5 to about 1.0 wt %, based on the weight of the salt dispersion.

15. The method of claim 1, wherein the alkaline earth metal compound is present in an amount of at least 25% above the stoichiometric amount required to neutralize the acid.

16. The method of claim 1, wherein the alkaline earth metal compound is present in an amount of at least 1000% more than the stoichiometric amount required to neutralize the acid.

17. The method of claim 1, wherein the incorporating occurs at a temperature from about 20 to about 50° C.

18. The method of claim 1, wherein the incorporating occurs in a Silverson in-line high shear low pressure mixer.

19. The method of claim 1, wherein the alkaline earth metal tallate dispersion has a bimodal particle size distribution of alkaline earth metal tallate particles in water.

20. The method of claim 19, wherein the bimodal particle size distribution exhibits a first maxima at about 10 to 30 microns and a second maxima at about 100 to 150 microns.

21. The method of claim 1, wherein the alkaline earth metal tallate dispersion exhibits a viscosity of less than about 500 cps after 120 days storage at a maximum temperature of 30° C.

22. The method of claim 1, comprising the further step of adding a post-formation stabilizer to the dispersion.

23. The method of claim 22, wherein the post-formation stabilizer is a surfactant which is the same as or different from the surfactant used to form the pre-emulsion, and is selected from the group consisting of anionic, cationic, and nonionic surfactants.

24. The method of claim 23, wherein the post-formation stabilizing surfactant is selected from the group consisting of dicarboxylic acid, sulfonate, and ether carboxylate anionic surfactants; quaternary ammonium cationic surfactants; and ethylene oxide:propylene oxide block and random polymeric non-ionic surfactants.

25. The method of claim 22, wherein the post-formation stabilizer is added in an amount of about 0.5 to 2.5 wt % of the tallate dispersion.

26. The method of claim 22, wherein the alkaline earth metal tallate dispersion exhibits a viscosity of less than about 500 cps after 60 days storage at a maximum temperature of about 50° C.

* * * * *